(12) United States Patent
Xie et al.

(10) Patent No.: US 10,639,001 B2
(45) Date of Patent: *May 5, 2020

(54) PUSH/TRACKING SEQUENCES FOR SHEAR WAVE DISPERSION VIBROMETRY

(71) Applicant: KONINKLIJKE PHILIPS N.V., Eindhoven (NL)

(72) Inventors: Hua Xie, Ossining, NY (US); Anna Teresa Fernandez, Eindhoven (NL); Michael R. Burcher, Cambridge (GB); Douglas Maxwell, Woodinville, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 891 days.

This patent is subject to a terminal disclaimer.

(21) Appl. No.: 14/818,339

(22) Filed: Aug. 5, 2015

(65) Prior Publication Data

US 2015/0335313 A1    Nov. 26, 2015

Related U.S. Application Data

(63) Continuation of application No. 13/379,741, filed as application No. PCT/IB2010/052852 on Jun. 23, 2010, now Pat. No. 9,125,547.

(Continued)

(51) Int. Cl.
*A61B 8/00* (2006.01)
*A61B 5/00* (2006.01)
*A61B 8/08* (2006.01)

(52) U.S. Cl.
CPC .............. *A61B 8/00* (2013.01); *A61B 5/0048* (2013.01); *A61B 5/0051* (2013.01); *A61B 8/085* (2013.01); *A61B 8/485* (2013.01); *A61B 8/5223* (2013.01)

(58) Field of Classification Search
CPC . G01S 7/52042; A61B 5/0048; A61B 5/0053; A61B 8/485; A61B 8/00
See application file for complete search history.

(56) References Cited

U.S. PATENT DOCUMENTS

| | | |
|---|---|---|
| 5,099,848 A | 3/1992 | Parker et al. |
| 2005/0165306 A1* | 7/2005 | Zheng ............... A61B 8/00 600/437 |

(Continued)

FOREIGN PATENT DOCUMENTS

| | | |
|---|---|---|
| EP | 154090 A1 | 6/2005 |
| FR | 2869521 A1 | 11/2005 |
| JP | 6273397 A | 9/1994 |

OTHER PUBLICATIONS

"Quantifying Elasticity and Viscosity from Measurement of Shear Wave Speed Dispersion" Chen et al, The Journal of Acoustical Society of America, vol. 115, No. 6, pp. 2781-2785, 2004.

(Continued)

*Primary Examiner* — Elmer M Chao

(57) ABSTRACT

Shear Wave Dispersion Vibrometry (SDUV) is performed such that, after a single instance of their push pulse (218), a plurality of tracking pulses (222) are issued to sample, more than once, each of a plurality of locations (120, 148) on an associated monochromatic shear wave (116) in sampling that at least one of scans the plural locations in separate passes and, with a pulse of the plural tracking pulses, samples multiple ones of the plural locations concurrently. In a supplementary aspect, phase difference, for a given moment, is determined by taking into account intersample delay (156), if the determination relies on samples that are taken at different times.

18 Claims, 7 Drawing Sheets

Related U.S. Application Data

(60) Provisional application No. 61/221,831, filed on Jun. 30, 2009.

(56) References Cited

U.S. PATENT DOCUMENTS

2007/0038095 A1* 2/2007 Greenleaf ............... A61B 8/00
600/438
2007/0049824 A1 3/2007 Konofagou et al.

OTHER PUBLICATIONS

"Error Estimates in Shear Wave Speed and Tissue Material Properties in Shear Wave Dispersion Ultrasound Vibrometry" Urban et al, 2007, IEEE Ultrasonics Symposium pp. 664-667
"Ultrasonic Imaging of Internal Vibration of Soft Tissue Under Forced Vibration" Yamakoshi et al, IEEE Transactions on Ultrasonics, Ferroelectronics and Frequency Control, vol. 37, No. 2, p. 45-53 1990.
Bouchard .R et al, "Image Quality Tissue Heating and Frame Rate Tradeoffs in Acoustic . . . " IEEE Transactions on Ultrasonics, Ferroelectrics and Frequency Control, IEEE US LNKD-DOI10 vol. 56, No. 1, Jan. 1, 2009 pp. 63-76.
Deffieux T. et al "Shear Wave Spectroscopy for In Vivo Quantification of Human . . . " IEEE Transactions on Medical Imaging, IEEE, vol. 28, No. 3. Mar. 2009 p. 313-322.
Muller M. et al "Quatitative Viscoelasticity Mapping of Human Liver Using . . . " Ultrasound in Medicine and Biology, vol. 35, No. 2, Feb. 1, 2009, p. 219-229.
Greenleaf, J.F., "6G-4 Measurement of Shear Wave Using Ultrasound and Kalman Filter With Large Background . . . " Ultrasonics Symposium 2006, IEEE, Oct. 1, 2006, p. 718-721.
Dahl, JJ, "A Parallel Tracking Method for Acoustic Radiation Force Impulse Imaging" IEEE Transactions on Ultrasonics, Ferroelectrics and Frequency Controol, IEEE, vol. 54, No. 2, Feb. 1, 2007, p. 301-312.

* cited by examiner

PUSH/TRACKING SEQUENCES FOR SHEAR WAVE DISPERSION VIBROMETRY

This application is a continuation application of U.S. patent application Ser. No. 13/379,741 filed Dec. 21, 2011, which is a national stage filing under 35 U.S.C. § 371(c) of International Appl. No. PCT/IB2010/052852, filed Jun. 23, 2010, which claims priority to U.S. Prov. Appl. No. 61/221,831, filed Jun. 30, 2009, the disclosures of which are incorporated herein by reference in their entirety.

The present invention is directed to measuring a shear wave and, more particularly, to doing so by Shear Wave Dispersion Vibrometry (SDUV).

Mechanical changes in living tissue correlate with pathological changes. As between healthy and pathological tissue, the shear elastic modulus (stiffness) and viscosity can vary significantly. With the advent of ultrasound elasticity imaging development over the past decade, many clinical studies have shown that tissue visco-elastic properties provide useful information to physicians for better cancer diagnosis and therapy assessment.

Shear Wave Dispersion Vibrometry (SDUV) is an acoustic radiation force based technique that measures tissue shear elasticity and viscosity by characterizing shear wave speed dispersion, i.e., by frequency. An application of this technique is the non-invasive measurement of liver stiffness to stage liver fibrosis and cirrhosis.

Interrogation by ultrasound, for purposes of medical imaging, often makes use of longitudinal waves. In body tissue, the ultrasound propagates in wave form. In effect, particles all along the propagation path vibrate, in place, back and forth, and the vibration occurs in the direction of propagation. The vibrations create compressions and rarefactions. These are modeled as the peaks and valleys of a sinusoid. Energy is conveyed to the target and back by means of the oscillatory particle movements.

An ultrasound shear (or transverse) wave, by contrast, is characterized by back and forth in-place movement that is perpendicular to the direction of propagation. Oscillation one way creates the peaks, and the other way creates the valleys.

Performing SDUV entails issuing a series of focused longitudinal-wave push pulses. They establish, at the focus, a shear wave whose direction of propagation is perpendicular to that of the push pulses. The focal depth has been selected so that the shear wave travels through a region of interest (ROI). A longitudinal-wave tracking pulse is issued to the ROI to assess, at the sampling point, the amplitude of the shear wave. This measurement is used in estimating the phase of the shear wave at the sampled location. To sample another location, another push pulse issues to the same pushing focus, followed by a tracking pulse to that location. This second cycle is needed, because the difference in phase between two points is used in the determining of elasticity and viscosity.

The period of time between issuance of the push pulse and issuance of the subsequent tracking pulse is equal in both cycles, which gives significance to the measurements as a means by which to determine location-based phase difference. It is the location-based phase difference which serves as a factor in a particular shear wave propagation speed estimation, and the resulting speed values over several wave frequencies are used in deriving elasticity and viscosity.

Conventionally, the SDUV sampling during each cycle is from a single location, as is described in two technical papers by the Mayo Clinic, because the tracking probe is essentially a piston-driven single-element transducer that does not have the steering capability The two technical papers are "Quantifying Elasticity and Viscosity from Measurement of Shear Wave Speed Dispersion," The Journal of the Acoustical Society of America, vol. 115, no. 6, pp. 2781-2785, 2004, to S. Chen, M. Fatemi, and J. F. Greenleaf and "Error Estimates in Shear Wave Speed and Tissue Material Properties in Shear Wave Dispersion Ultrasound Vibrometry", 2007 IEEE Ultrasonics Symposium, pp. 664-667, to M. W. Urban, S. Chen and J. F. Greenleaf.

Both papers describe actual experiments.

A formula for calculating wave propagation speed, using the difference between two measurements as the phase difference, appears in both papers, as formula (4). The underlying calculations are shown in more detail in the publication authored by Urban.

Another Mayo Clinic publication, U.S. Patent Publication No. 2007/0038095, entitled "Ultrasound Vibrometry," to J. F. Greenleaf and S. Chen further proposes steering a beam to, during the same cycle: a) sample from two or more locations; and b) take two or more phase measurements.

For the proposed method, the patent publication applies the same exact formula.

The instant inventors have observed that the prior art discussed above, appears not to cite actual experiments, not to specify or suggest any particular spatiotemporal sampling scheme in connection with its proposal, and not to disclose or suggest any modification of the propagation speed formula that would take into account intersample delay. The inventors have further observed that not taking into account such delay when sampling from a plurality of locations during the same cycle can lead to significantly erroneous results.

More generally, one main challenge associated with detecting radiation-force-induced shear waves using SDUV is the relatively low amplitude vibration (axial displacement is on the order of 10 µm). The sampling measures the amplitude of the shear wave at a given or current location in the ROI. However, system electronic noise and patient motion such as cardiac or respiratory motion will contribute significant noise to shear wave displacement estimation.

To greatly reduce the severe effects of noise, more than two push/tracking sequences can be fired in order to probe spatiotemporal evolution of the shear displacements at multiple lateral locations. Least-squares fitting algorithms can be applied to multiple phase delay estimates to obtain more robust speed estimates.

SDUV push pulses focus on the same excitation location in the tissue. The repeated acoustic exposure from multiple push/tracking sequences could result in accumulated local tissue heating. This is especially true when the time delay between successive excitations is less than the tissue cooling time. The tissue cooling time will depend on the perfusion of the organ examined, etc. The thermal safety of SDUV is one of the key concerns that researchers have to address before this technique can be applied in clinical studies. For diagnostic ultrasound, the Food and Drug Administration (FDA) requires the Thermal Index (TI) to be less than 6 (tissue heating<6° C.). Although the thermal increase from a single SDUV push is about 0.1° C.-0.2° C., and the exposure level of SDUV is significantly below the threshold of tissue damaging, the cumulative effects of SDUV may impose risk to tissue and transducer heating.

It accordingly is desirable to get as much accomplished as possible in the way of affording robust measurement, but with as few push/tracking sequences as possible, so that adverse thermal effects are avoided.

In one aspect, a novel shear wave dispersion vibrometry (SDUV) method includes, after a single instance of their push pulse, issuing tracking pulses to sample, more than once, each of a number of locations on an associated monochromatic shear wave. This is done in sampling that scans the locations in separate passes and/or samples, with a pulse, multiple ones of the locations concurrently.

In a supplementary aspect, phase difference, for a given moment, is determined by taking into account intersample delay. This is done if the determination relies on samples that are taken at different times.

As a further aspect, the determining entails calculating the difference using two of the differently-timed samples, and adding, to the calculated difference, an intersample-delay-based phase correction reflecting, for the monochromatic shear wave, propagation that occurred temporally between the taking of the two samples.

In an alternative aspect, the calculated difference and the correction are numbers whose signs are opposite when the scanning from one of the two samples to the other occurs in a direction opposite to that in which the wave propagates.

In an additional aspect, the correction is directly proportional to an angular frequency of said wave and to a delay between the taking of said two samples.

In one version, the sampling occurs, pass-to-pass, in opposite directions, and the taking into account includes combining respective measurements from two oppositely-directed passes to cancel out the intersample delay.

In a still further aspect, the separate passes are made in a same direction.

In some embodiments, the tracking pulses are steered, serially, pulse-by-pulse.

In certain embodiments, the sampling includes sampling, by means of a pulse, multiple locations concurrently.

In particular aspects of the invention, the pulse is targeted to more than one of the locations simultaneously.

In a sub-aspect, the tracking pulse is targeted to all of the locations simultaneously.

In yet another aspect, receiving A-lines from corresponding ones of the locations are concurrently received, in response to one of the tracking pulses.

In a different aspect, a reference pulse is emitted when there are no push pulse vibrations, and data echoed from the reference pulse is compared to data echoed from a tracking pulse, in calculating an amplitude of the wave.

According to some versions, an article of manufacture includes a machine-accessible medium having instructions encoded thereon for enabling a process to perform a method set forth above.

Likewise, in particular embodiments, a computer software product for performing shear wave dispersion vibrometry (SDUV) comprises a computer readable medium embodying a computer program that includes instructions executable by a processor to perform a method set forth above.

Similarly, in accord with one aspect, an ultrasound device configured for SDUV includes a transducer arrangement for performing a method set forth above.

In a yet further aspect, the device is configured for, automatically without user intervention, based on an image depth and sample acquisition frequency, switching from a single A-line receiving mode per sample to a multi-A-line receiving mode per sample.

Details of the novel SDUV push/tracking scheme are set forth further below, with the aid of the following drawings.

Figure 1:
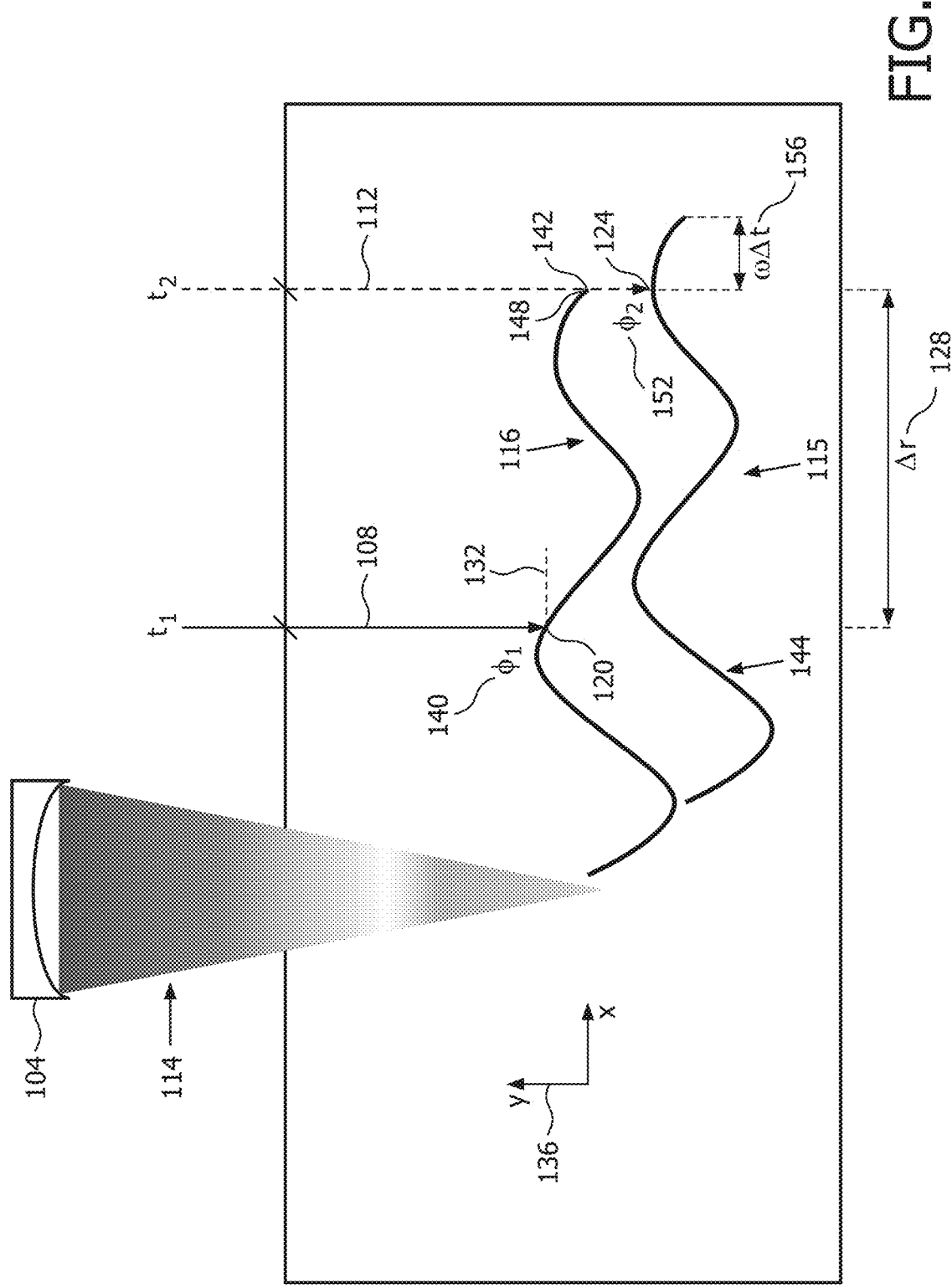
FIG. 1 is a schematic diagram exemplary of a consecutive two of the SDUV samples, in accordance with the present invention.

FIG. 1 depicts, by way of illustrative and non-limitative example, a relation between two consecutive SDUV samples. An ultrasound pushing probe 104 is shown, along with first and second tracking pulses 108, 112 issued, respectively, at sampling times t1, t2, by an ultrasound tracking probe (not shown). The pushing probe 104 sends out a series of focused pushing pulses (or "pushes") 114 to establish a shear wave 115, a frequency component of which (or "monochromatic shear wave") is represented by a first trace 116. Tissue vibrates along the y-direction and the shear wave propagates along the x-direction.

Two separate probes can be used for pushing and tracking respectively. However this type of bulky configuration is not practical for clinical applications.

In addition, in the case of separate single-element transducers, it requires repeated firing of the pushing pulses in order to measure the shear wave phase delay at different lateral positions, resulting in repeated tissue heating.

If, on the other hand, tracking is implemented with an array transducer, the need for repeated pushes is alleviated in accordance with the proposal herein.

Moreover, one single array transducer can serve both functions of pushing and tracking. A dual-purpose single array transducer would make the system more compact and easier to control. However this configuration needs more hardware and software support to ensure it is feasible to generate acoustic radiation force and image the resulting shear wave 115 by a single transducer. The single transducer can be a single-row array (1D transducer) or multiple-row array (2D transducer) that allows for lateral and elevation pushing and or tracking pulse locations.

Advanced 2D array technology will allow tracking pulses to be sent in 3D dimensions; however, the following discussion relates to tracking tissue motion in the axial-lateral plane. The same treatment applies to the axial-elevation plane, without loss of generality.

The tracking pulses 108, 112 are targeted to respective locations 120, 124 spatially separated by a distance 128 of $\Delta r$. The distance 128 is typically in the millimeter range, because the shear wave 115 attenuates with propagation distance. An amplitude 132, as represented on the y-axis 136, is measured. Based on the amplitude 132, a phase 140 of $\Phi_1$ at the location 120 can be derived, provided the Nyquist threshold is met regarding sampling frequency. The Nyquist threshold can be met by multiple sampling passes over the location 120 with sufficient frequency.

If the sampling times t1, t2 were simultaneous, return data, i.e., echo data, from the tracking pulse 112 would have suggested a phase 142 corresponding to sampled point 148 on the first waveform 116.

However, the sampling times t1, t2 are not simultaneous if tracking pulses are sequentially fired for these two locations 120 and 124.

In fact, by the time $t_2$, the shear wave component 116 has propagated forward, as a waveform having a frequency component represented by a second trace 144.

The corresponding sampled phase 152 of $\Phi_2$, on the second trace 144, differs from the phase 140 of $\Phi_1$, on the first trace 116, by a phase difference of $\Delta\Phi=\Phi_2-\Phi_1$.

As seen from FIG. 1, $\Delta\Phi$ is less than the difference between the phases 140, 142 that simultaneous tracking pulses would have fetched.

As further seen from FIG. 1, $\Delta\Phi$ is smaller by an intersample-delay-based phase correction 156 of $\omega\Delta t$, "$\omega$" representing the angular frequency of the monochromatic shear wave 116, with "$\Delta t$" signifying the delay between the taking, at the respective sampling times t1, t2, of the two samples.

Yet it is the difference between the phases 140, 142 that, along with $\omega$ and $\Delta r$, define the propagation speed of the shear wave frequency component 116.

That difference is calculated by adding, to the phase difference $\Delta\Phi$, the intersample-delay-based phase correction 156 of $\omega\Delta t$.

Figure 2:
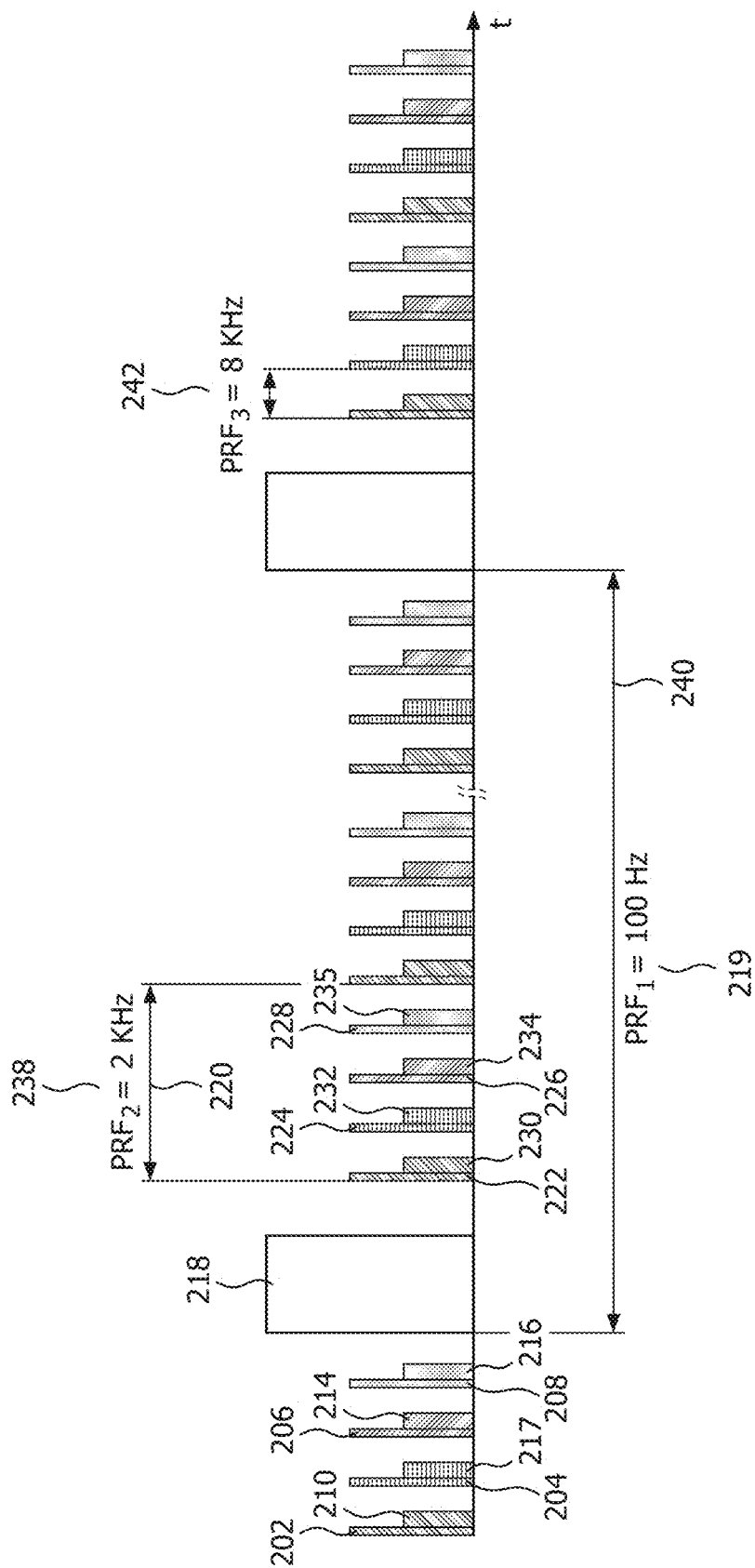
FIG. 2 is a timeline of an example representative of sequential SDUV tracking, in accordance with the present invention.

FIG. 2 depicts sequential SDUV tracking as proposed herein. Before any push pulses 114 vibrate the region of interest (ROI), reference tracking pulses 202, 204, 206, 208 issue, targeted at respective sampling locations x1, x2, x3, x4. The locations x1, x2, x3 and x4 are aligned radially out from the excitation point for pushing, i.e., in a propagation direction of the shear wave 115. The pulses 202, 204, 206, 208 are each followed respectively by their echoes 210, 212, 214, 216. The shear wave 115 is then established at a location x0, i.e., the site of the excitation point. This is done by an initial series (not shown in FIG. 2) of push pulses 218 that are fired at a push frequency 219 which might typically be approximately 100 Hz. A tracking-sequence-initiating onset of the push pulses 218 can issue once the wave 115 has been established. A pass 220 of tracking pulses 222, 224, 226, 228 follows, steered, serially, pulse-by-pulse. The tracking pulses 222, 224, 226, 228 are emitted, each followed by its respective echo 230, 232, 234, 236. The pass 220 issues at a same-location tracking frequency 238 of 2 KHz. Accordingly, 20 passes 220 can follow the push 218. Also, the same-location tracking frequency 238 of 2 kHz allows phase measurement of components 116 of frequencies of up to about 1 kHz, the Nyquist threshold. Each of the tracking pulses 222, 224, 226, 228 can serve to simultaneously provide measurement of each of the frequency components, within the inherent limits of the Nyquist threshold.

Regular B-mode imaging is utilized, i.e., the tracking pulses 222, 224, 226, 228 are electronically focused and steered back and forth laterally at different locations x1, x2, x3, x4 between two adjacent pushing pulses 218. Receiving A-lines at different locations x1, x2, x3, x4 are therefore formed sequentially. The number of transmission lines within each B-mode frame should be limited so that the sampling PRF (pulse repetition frequency) for the shear wave 115 is high enough. As seen in FIG. 2, for example, for each location x1, x2, x3, x4, the same-location tracking frequency 238 is 2 KHz ($PRF_2$), while the transmission A-line frequency 242 is 8 KHz ($PRF_3$).

Advantageously, merely a single push/tracking sequence 240 is needed to obtain all of the SDUV information needed for shear wave speed estimation. Faster data acquisition, as is being proposed herein, is a key requirement to advance the technique of SDUV from a single-point "virtual biopsy" tool to a possible real-time imaging modality. In the meantime, the heat generated in the tissue and transducer can be decreased while maintaining the number of lateral locations x1, x2, x3, x4, ... observed for shear wave tracking Another advantage of this invention is that it can further reduce noise in shear wave displacement estimation, especially to avoid large temporal-scale noise such as respiratory motion that tissue experiences during different pushing/tracking sequences 240.

For the tracking pulses of the push/tracking sequence, a "single instance of their push pulse" is defined herein as the push pulse that temporally immediately precedes the tracking pulses.

Figure 3:
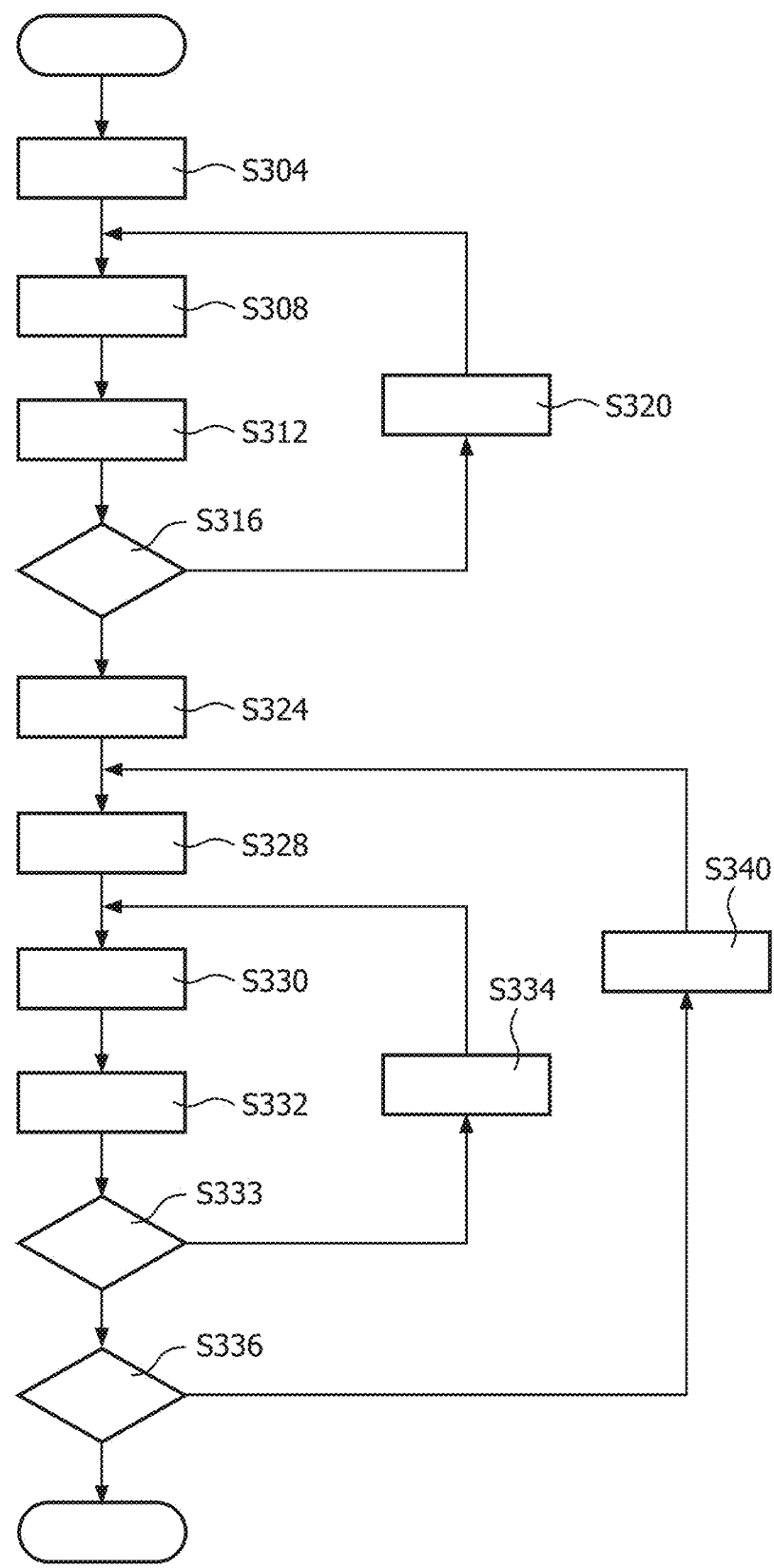
FIG. 3 is a flow chart corresponding to the timeline of FIG. 2, according to the present invention.

FIG. 3 is a flow chart corresponding to the timeline of FIG. 2. Focus is set to the first location x1 (step S304). A current tracking reference pulse 202 is emitted (step S308). Its echo 210 follows (step S312). If there are more locations (i.e., x2, x3, x4) to be measured (step S316), the focus is steered to the next location (step S320), and processing returns to the tracking reference pulse emitting step S308 with that next location as the current location. On the other hand, if there are no further locations to be measured (step S316), the push pulse 218 is fired successively to establish the shear wave 115 (step S324). The focus is then set to the first location x1 (step S328). The current tracking pulse 222 is emitted (step S330), and its echo 230 is returned (step S332). If there are more tracking pulses (i.e., 224, 226, 228) to issue in the current pass 220 (step S333), the focus is set to the corresponding next location (step S334) and processing returns to the tracking pulse emitting step S330 with the next location as the current location. Otherwise, if there is no next tracking pulse to be emitted, query is made as to whether another pass is to be made over the locations x1, x2, x3, x4 (step S336). If a next pass is to be made, that next pass is made the current pass (step S340), and processing returns to the beginning of the next pass 220 at the step S328. If, however, there is no next pass 220 to be made (in the current push/tracking sequence 240), sampling is completed. A single push/tracking sequence 240 suffices, in the instant proposed technique, to provide all of the sampling needed for SDUV determination of shear wave speed and, in practical embodiments, for calculation of tissue elasticity and viscosity.

Figure 4:
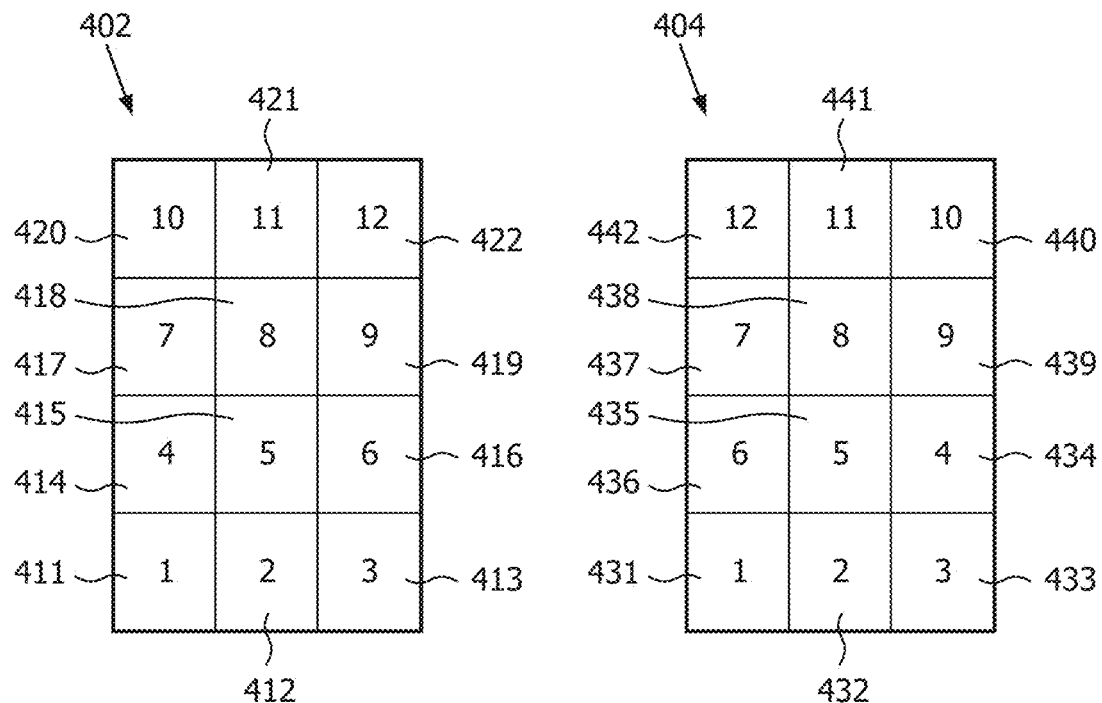
FIG. 4 is a conceptual diagram of two possible SDUV spatiotemporal sampling schemes, in accordance with the present invention.

Two possible SDUV spatiotemporal sampling schemes 402, 404, as proposed herein, are portrayed in FIG. 4.

For the uniform-direction sampling scheme 402, four passes 220 are shown. Each is over three locations x1, x2, x3. Each is represented in FIG. 4 in a left-to-right direction. The numbers 1 through 12, denoted 411 through 422, correspond to the order in which the sampling occurs. Separate passes 220 are made in the same direction.

The alternating-direction sampling scheme 404 likewise is shown for four passes 220 over the three location x1, x2, x3. However, in contrast to the uniform-direction sampling scheme 402, the alternating-direction sampling scheme 404 alternates the direction of scanning with each pass 220. The numbers 1 through 12, denoted 431 through 442, correspond to the order in which the sampling occurs. Sampling in opposite directions is an alternative to adding in the intersample-delay-based phase correction 156, as will be discussed in more detail further below.

The same-location tracking frequency 238 at the location x2 is the same in both sampling schemes 402, 404. For the off-center locations x1, x3 in the alternating-direction sampling scheme 404, sampling is temporally irregular. However, the Nyquist threshold holds for irregular sampling. It is the average sampling frequency that is subject to the threshold. Since the average sampling frequency is the same for all of the locations x1, x2, x3 of both the schemes 402, 404, either of the schemes is implementable in a manner that avoids aliasing.

Figure 5:
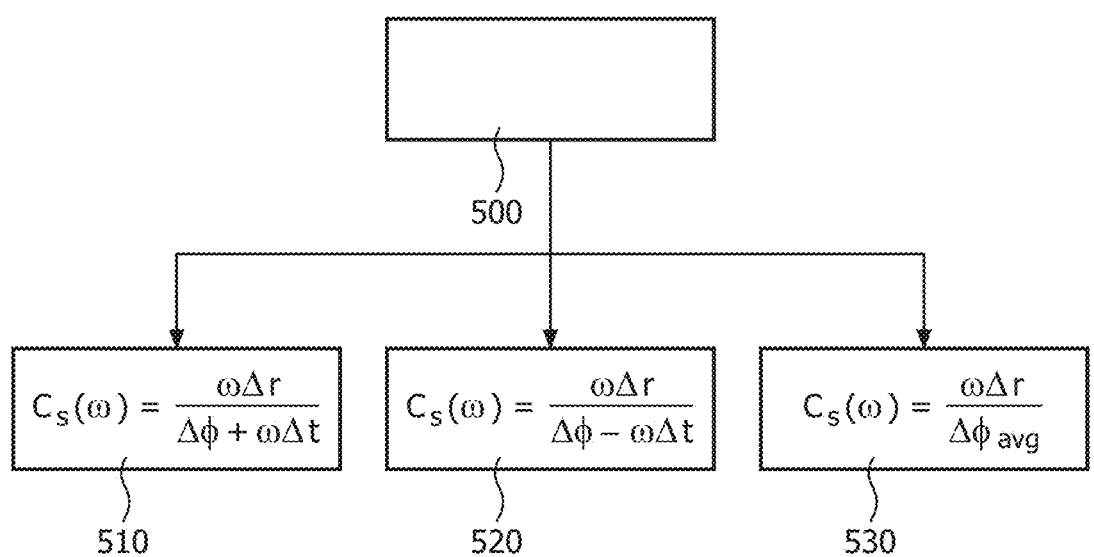
FIG. 5 is a flow chart showing alternative SDUV shear-wave-propagation-speed algorithms for respective sampling orders, in accordance with the present invention.

FIG. 5 demonstrates alternative SDUV shear-wave-propagation-speed algorithms 500 for respective orders in which samples are taken at different times t1, t2.

For scanning in the same direction in which the shear wave 115 propagates, the forward-scan formula 510 applies. A derivation of the formula 510 is as follows:

$c_s(\omega) = \lambda f$, where $c_s$ is propagation speed, $\lambda$ is the wavelength, and $f$ is the wave's frequency.

Also, $\omega = 2\pi f$, and $\Delta r = \lambda \Delta \Phi / 2\pi$, where $\Delta \Phi$ represents the phase difference, for a given moment, between the two samples taken simultaneously.

All parameters are assumed to be positive.

Substituting values yields $$c_s(\omega) = \frac{\omega \Delta r}{\Delta \phi}$$

To account for the intersample delay between the two differently-timed samples taken at the times t1, t2, the intersample-delay-based phase correction 156 of $\omega \Delta t$ is added to $\Delta \Phi$, as explained above in connection with FIG. 1. The correction 156 is directly proportional to an angular frequency $\omega$ of the wave 115, particularly of the wave component 116 whose speed is currently being measured, and to the delay $\Delta t$ between the taking of the two samples.

For scanning in the direction opposite to that in which the shear wave 115 propagates, the reverse-scan formula 520 applies. In the reverse-scan formula 520, the sign of the intersample-delay-based phase correction 156 of $\omega \Delta t$ is opposite to that of the calculated (phase) difference $\Delta \Phi$ which is for a given moment. The reason for making the correction 156 negative is based on reasoning analogous to the above explanation here and in relation to FIG. 1. The intersample-delay-based phase correction 156 reflects, for the monochromatic shear wave 116, propagation that occurred temporally between the taking of the two differently-timed samples at the times t1, t2, respectively.

If scanning in one pass 220 is in a direction opposite to that of the scanning in another, e.g., subsequent, pass, the respective $\Delta \Phi$ measurements on the same two locations x1, x2 can be averaged to cancel out intersample delay. This assumes that the intersample delay between the two locations x1, x2 is equal in both passes. If the assumption holds, the denominator of formula 530 indicates that the intersample-delay-based phase corrections 156, if determined, would be canceled out by the averaging of the denominators of the single-scanning direction formulas 510, 520. Accordingly, the corrections 156 need not be computed, and are unnecessary in using the formula 530.

Figure 6:
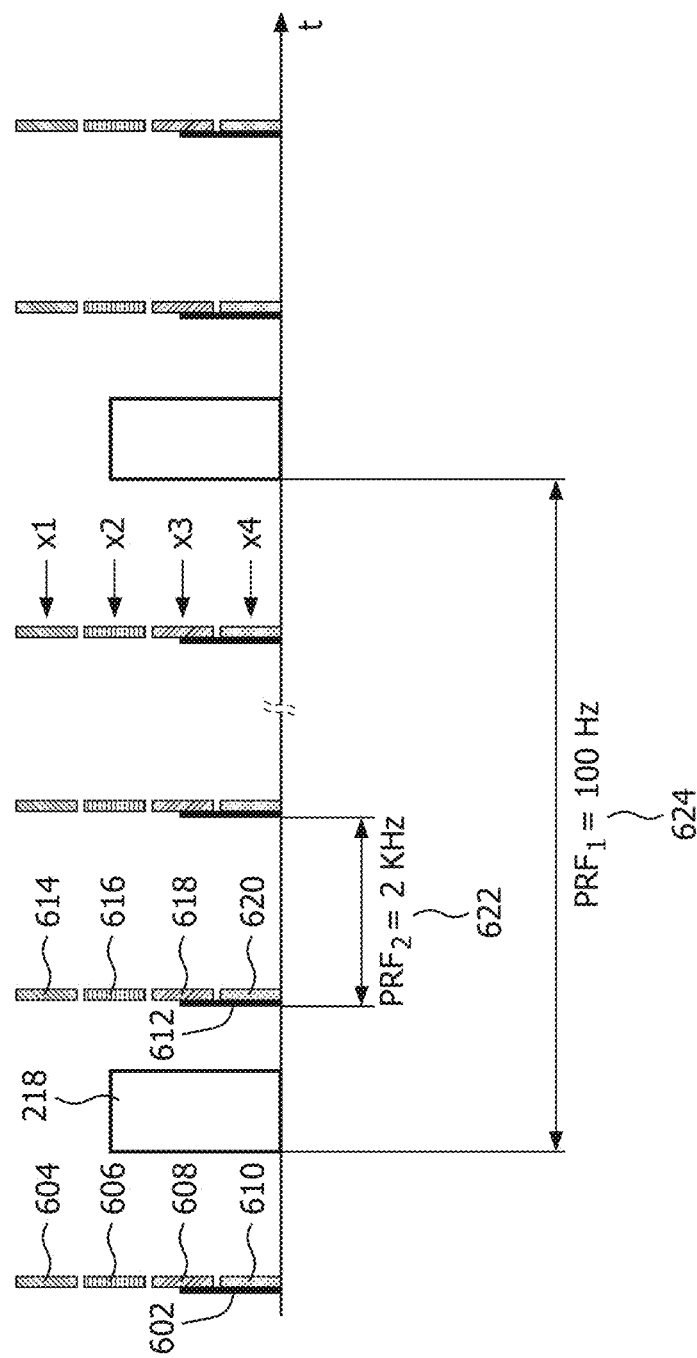
FIG. 6 is a timeline of an example representative of parallel SDUV tracking.

Parallel SDUV tracking, as opposed to the sequential tracking of FIG. 2, is portrayed in FIG. 6, the portrayal representing one possible embodiment. In parallel tracking, a tracking pulse is targeted to more than one, and in fact to all, of the plurality of locations simultaneously.

In order to monitor the shear wave propagation created by the pushing pulses 218, the same-location tracking frequency 238 at each detection point or location x1, x2, x3, x4 should be set high enough to satisfy the Nyquist limit, with respect to the highest harmonic frequency under analysis. Following the example scenario described above and as shown in FIG. 6, each detection point is tracked by the same-location tracking frequency 238 of 2 KHz, while the four detection points or locations x1, x2, x3, x4 are sequentially scanned with the transmission A-line frequency 242 is 8 KHz. If more detection points are desired, the ultrasound system will be required to transmit at an even higher PRF, which might be difficult or impossible to realize (physically limited by the ultrasound travel time to and back from the maximum imaging depth) under this "sequential tracking" mode.

To overcome this problem a second method, called "parallel tracking," is proposed herein, and is portrayed below in an exemplary embodiment.

In parallel receiving B-mode, broad transmission beams are each weakly focused. They are, between respective pushes 218, emitted repeatedly to the same region spanning different locations x1, x2, x3, x4. For a given single detection transmission, multiple receiving A-lines are parallel-beamformed by a multi-line beamformer using the backscattered signals received by the array at once. In other words, multiple ones of the plurality of locations are sampled concurrently with each tracking pulse.

A tracking reference transmission 602 is sent. Multiple parallel receiving reference A-lines 604, 606, 608, 610 are formed for respective locations x1, x2, x3, x4. After the push pulse 218 at the excitation point x0, a number of tracking transmission pulses 612 are issued, each followed by respective parallel receiving A-lines 614, 616, 618, 620 to the corresponding locations x1, x2, x3, x4. The tracking transmission pulses 612 and their respective parallel receiving A-lines 614, 616, 618, 620 are repeated with a parallel tracking frequency 622 of 2 kHz during the parallel push/tracking sequence 624.

If desired, more receiving A-lines can be added here to increase spatial sampling accuracy without lowering the tracking PRF, as long as the system supports broader transmission and a high-order multi-line receive beamformer. Similar to the sequential method portrayed above in FIGS. 2 and 3, the parallel tracking method does not require repeated firing of the focused ultrasound at the shear wave excitation origin. It enables shear wave speed estimation to be implemented through one single push/tracking sequence.

In the parallel tracking method, because the detection pulse covering different lateral locations x1, x2, x3, x4 is emitted at one single shot, the displacement estimates 132 at different lateral locations are sampled concurrently. In this case, there is no need to make any compensation. The shear wave speed should be estimated simply using the formula:

$$c_s(\omega) = \frac{\omega \Delta r}{\Delta \phi}. \qquad \text{(formula 540)}$$

Of course, transmitting broader beams 612 with weak focus will degrade the image spatial resolution at the focus. In the extreme case of plane wave transmission, parallel tracking may produce displacement estimates with slightly lower SNR than the sequential tracking. If SNR is a very critical issue or the ultrasound system only is equipped with a low-order multi-line beamformer, the "sequential tracking and the "parallel tracking" methods can be combined into a "hybrid tracking" method.

Figure 7:
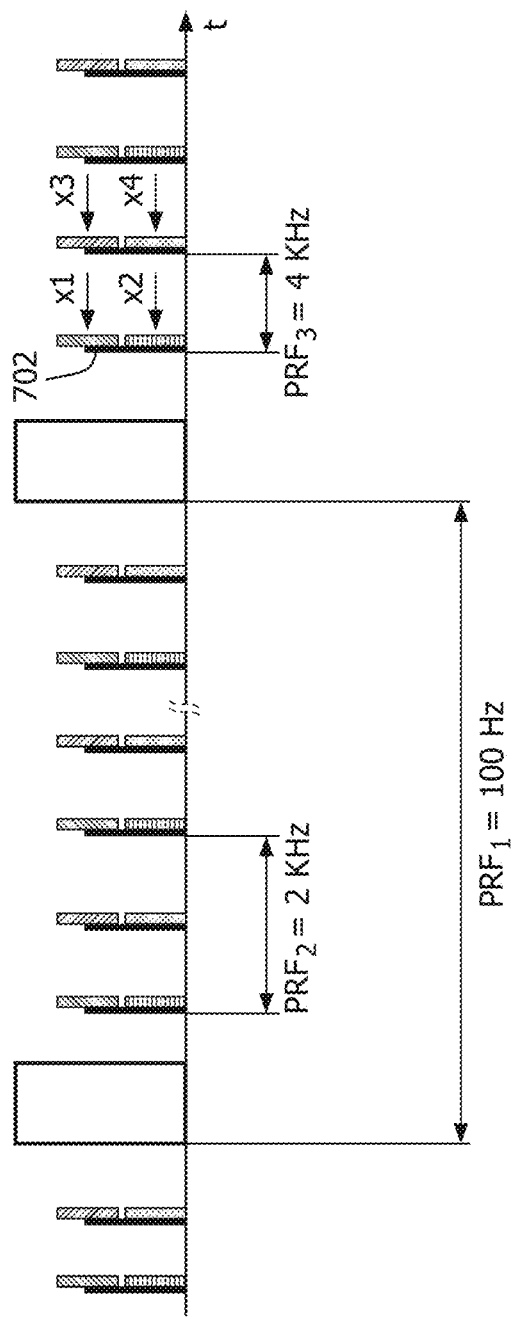
FIG. 7 is a timeline of an example representative of a combination of SDUV sequential and parallel tracking, according to the present invention.

FIG. 7 is a timeline of an example representative of a combination of SDUV sequential and parallel tracking.

The sequential and parallel tracking is similar to the parallel tracking, except that some of the locations, here x1 and x2 are sampled simultaneously (as by a tracking transmission pulse 702), yet locations x1, x2 are sampled sequentially with respect to the locations x3, x4.

In this scenario, a 2X multiline beamformer suffices for parallel tracking. The tracking PRF for individual point is 2 KHz ($PRF_2$), while the ultrasound system transmission PRF is 4 KHz ($PRF_3$). When calculating the shear wave speed, formula 540, shown above, should be used if points x1 and x2 are analyzed. In contrast, the appropriate formula 510, 520, 530 should be used if points x1 and x3 are analyzed.

Figure 8:
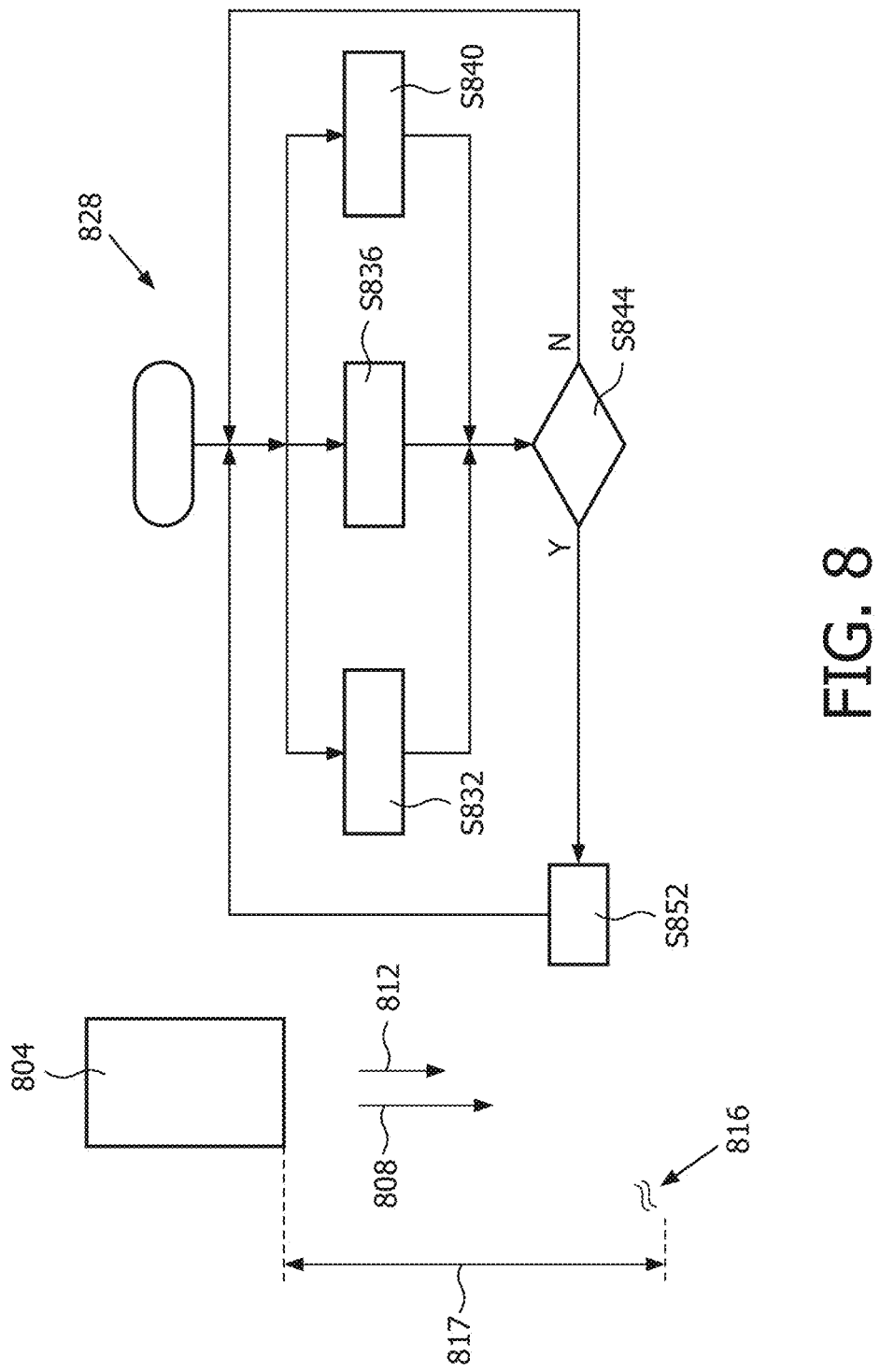
FIG. 8 is a combination flow chart and schematic diagram of a type of automatic switching between multi-line and single-line receiving modes, in accordance with the present invention.

FIG. 8 is a combination flow chart and schematic diagram of a type of automatic switching between multi-line and single-line receiving modes, in accordance with the present invention.

An ultrasound probe 804 transmits tracking pulses 808, 812 to respective locations in a ROI 816, here an organ or blood vessel, at a maximum image depth 817. The transmission in a multi-line receiving mode 820, as shown in FIG. 6, or in a single-line receiving mode 824, as in FIG. 2.

A monitoring process 828 checks the maximum image depth 817 (step S832), the transmission A-line frequency 242 (step S836), and a current mode 836 (step S840). If the maximum image depth 817 and the transmission A-line frequency 242 are high enough, the speed of sound through tissue may pose a limit that requires switching from the single-line receiving mode 824 to the multi-line receiving mode 820. Likewise, a transition may be made from the multi-line receiving mode to the single-line receiving mode, depending on whether the pace of signaling can be accommodated. If the switch is indicated (step S844), the current mode 836 is swapped with a new mode 848 (step S852), before processing returns for re-checking, after a delay, at the steps S832, S836, S840.

Shear Wave Dispersion Vibrometry (SDUV) is performed such that, after a single instance of their push pulse, a plurality of tracking pulses are issued to sample, more than once, each of a plurality of locations on an associated monochromatic shear wave in sampling that at least one of scans the plural locations in separate passes and, with a pulse of the plural tracking pulses, samples multiple ones of the plural locations concurrently. In a supplementary aspect, phase difference, for a given moment, is determined by taking into account intersample delay, if the determination relies on samples that are taken at different times.

An innovative SDUV push/tracking scheme can decrease tissue heating by limiting the number of acoustic radiation force excitations 218.

It should be noted that the above-mentioned embodiments illustrate rather than limit the invention, and that those skilled in the art will be able to design many alternative embodiments without departing from the scope of the appended claims. For example, more or fewer locations than shown in the drawings may be sampled in the various embodiments. Also, tracking reference pulses may be foregone, and replaced by cross-correlation between the repeated A-lines for a location in order to determine wave amplitude. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable medium. The mere fact that certain measures are recited in mutually different dependent claims does not indicate that a combination of these measures cannot be used to advantage.

What is claimed is:

1. A method for analyzing a shear wave, the method comprising:
   generating a push pulse focused on an excitation location in a region of interest, wherein the push pulse is arranged to establish a shear wave;
   sampling a plurality of target locations along the shear wave, the plurality of target locations aligned radially out from the excitation location, wherein the sampling comprises (i) scanning, the plurality of target locations with a plurality of tracking pulses, and (ii) obtaining a plurality of samples from at least some of the plurality of target locations at the same time; and
   determining a phase difference between two locations along the shear wave by subtracting a first sampled phase from a second sampled phase, wherein the first sampled phase and second sampled phase are acquired from two samples in the plurality of samples obtained at different times, and adding an intersample-delay-based phase correction, wherein the intersample-delay-based phase correction is directly proportional to an angular frequency of the shear wave and to a delay between the obtaining of the two samples.

2. The method of claim 1, wherein the intersample-delay-based phase correction reflects propagation of the shear wave that occurred temporally between the obtaining of the two samples.

3. The method of claim 2, wherein the phase difference and the intersample-delay-based phase correction are numbers whose signs are opposite when the scanning from one target location of the two samples to the other target location occurs in a direction opposite to that in which the shear wave propagates.

4. The method of claim 1, wherein the sampling comprises scanning in a pass-to-pass manner and in opposite directions for each scanning pass.

5. The method of claim 1, wherein the tracking pulses are steered serially and pulse-by-pulse.

6. The method of claim 1, wherein the sampling of each of the plurality of target locations comprises using a single tracking pulse of the plurality of tracking pulses.

7. The method of claim 1, wherein the sampling comprises targeting one tracking pulse of the plurality of tracking pulses to more than one of the plurality of target locations simultaneously.

8. The method of claim 1, further comprising concurrently receiving, in response to one of the plurality of tracking pulses, a plurality of receiving A-lines from corresponding target locations in the plurality of target locations.

9. The method of claim 1, further comprising: emitting a reference pulse when there are no push pulse vibrations; and, calculating an amplitude of the shear wave by comparing data echoed from the reference pulse to data echoed from a tracking pulse of the plurality of tracking pulses.

10. A system for analyzing a shear wave, the system comprising a computer program including instructions, which when executed by a processor circuit, cause the system to perform the following steps:
- generate, using a transducer probe, a push pulse focused on an excitation location in a region of interest, wherein the push pulse is arranged to establish a shear wave;
- sample a plurality of target locations along the shear wave, the plurality of target locations aligned radially out from the excitation location, wherein the sampling comprises (i) scanning, the plurality of target locations with a plurality of tracking pulses, and (ii) obtaining a plurality of samples from at least some of the plurality of target locations at the same time; and
- determine a phase difference between two locations along the shear wave by subtracting a first sampled phase from a second sampled phase, wherein the first sampled phase and second sampled phase are acquired from two samples in the plurality of samples obtained at different times, and adding an intersample-delay-based phase correction, wherein the intersample-delay-based phase correction is directly proportional to an angular frequency of the shear wave and to a delay between the obtaining of the two samples.

11. The system of claim 10, wherein the intersample-delay-based phase correction reflects propagation of the shear wave that occurred temporally between the obtaining of the two samples.

12. The system of claim 11, wherein the phase difference and the intersample-delay-based phase correction have opposite signs when the scanning from one target location of the two samples to the other target location occurs in a direction opposite to that in which the shear wave propagates.

13. The system of claim 1, wherein the instructions when executed further cause the system to scan the plurality of locations in a pass-to-pass manner and in opposite directions for each scanning pass.

14. The system of claim 10, wherein the instructions when executed further cause the system to steer the tracking pulses are serial and pulse-by-pulse.

15. The system of claim 10, wherein the instructions when executed further cause the system to use a single tracking pulse of the plurality of tracking pulses.

16. The system of claim 10, wherein the instructions when executed further cause the system to target one tracking pulse of the plurality of tracking pulses to more than one of the plurality of target locations simultaneously.

17. The system of claim 10, wherein the instructions when executed further cause the system to concurrently receive, in response to one of the plurality of tracking pulses, a plurality of receiving A-lines from corresponding target locations in the plurality of target locations.

18. The system of claim 10, wherein the instructions when executed cause the system to emit a reference pulse when there are no push pulse vibrations; and calculate an amplitude of the shear wave by comparing data echoed from the reference pulse to data echoed from a tracking pulse of the plurality of tracking pulses.

* * * * *